(12) United States Patent
Chang et al.

(10) Patent No.: US 11,168,298 B2
(45) Date of Patent: Nov. 9, 2021

(54) FILTER DEVICE FOR CAPTURING TARGET CELL AND TARGET CELL COLLECTING METHOD USING THE SAME

(71) Applicant: KOREA INSTITUTE OF MACHINERY & MATERIALS, Daejeon (KR)

(72) Inventors: Sunghwan Chang, Daejeon (KR); Jung Yup Kim, Daejeon (KR); Hyoun-Hyang Park, Daejeon-si (KR); Yeong-Eun Yoo, Seoul (KR)

(73) Assignee: KOREA INSTITUTE OF MACHINERY & MATERIALS, Daejeon (KR)

(*) Notice: Subject to any disclaimer, the term of this patent is extended or adjusted under 35 U.S.C. 154(b) by 399 days.

(21) Appl. No.: 16/074,474

(22) PCT Filed: Mar. 30, 2017

(86) PCT No.: PCT/KR2017/003480
§ 371 (c)(1),
(2) Date: Aug. 1, 2018

(87) PCT Pub. No.: WO2017/171426
PCT Pub. Date: Oct. 5, 2017

(65) Prior Publication Data
US 2019/0062691 A1 Feb. 28, 2019

(30) Foreign Application Priority Data
Mar. 30, 2016 (KR) .......................... 10-2016-0038357

(51) Int. Cl.
B01D 39/16 (2006.01)
B01D 25/12 (2006.01)
(Continued)

(52) U.S. Cl.
CPC ........... *C12M 47/04* (2013.01); *B01D 25/003* (2013.01); *B01D 25/12* (2013.01); *B01D 33/01* (2013.01);
(Continued)

(58) Field of Classification Search
CPC ...... C12M 47/04; C12M 33/14; C12M 3/067; C12M 3/06; C12M 47/12; C12M 3/062;
(Continued)

(56) References Cited

U.S. PATENT DOCUMENTS 3,255,110 A * 6/1966 Peeler .................. C10M 135/36
508/251
4,310,416 A * 1/1982 Tanaka .................. B01D 61/28
210/321.75
(Continued)

FOREIGN PATENT DOCUMENTS

| JP | 2007-003478 | | 1/2007 | |
|---|---|---|---|---|
| KR | 10-2011-0115476 | | 10/2011 | |
| KR | 10-2012-0042533 | | 5/2012 | |
| KR | 10-1697457 | | 1/2017 | |
| RU | 2136348 | * | 9/1999 | ............. B01D 27/00 |

*Primary Examiner* — Joseph W Drodge
(74) *Attorney, Agent, or Firm* — Lex IP Meister, PLLC

(57) ABSTRACT

The present invention relates to a filter device for capturing a target cell and a target cell collecting method using the same. A filter substrate by which a target cell is captured is formed of an elastic material. When blood passes, the size of a lattice hole of the filter substrate by which the target cell is captured is reduced. When the blood completely passes, the size of the lattice hole of the filter substrate by which the target cell is captured is restored, so that a destruction rate of the target cell may be reduced and a collect rate of the target cell may be increased.

9 Claims, 16 Drawing Sheets

(51) Int. Cl.
*B01D 33/01* (2006.01)
*C12Q 1/24* (2006.01)
*C12M 1/00* (2006.01)
*B01L 3/00* (2006.01)
*B01D 25/00* (2006.01)
*C12M 3/06* (2006.01)
*C12M 1/26* (2006.01)
*G01N 1/40* (2006.01)

(52) U.S. Cl.
CPC ....... *B01D 33/015* (2013.01); *B01D 39/1692* (2013.01); *B01L 3/50255* (2013.01); *C12M 3/06* (2013.01); *C12M 3/067* (2013.01); *C12M 33/14* (2013.01); *C12Q 1/24* (2013.01); *B01D 2201/186* (2013.01); *B01D 2201/202* (2013.01); *B01D 2239/065* (2013.01); *B01L 3/505* (2013.01); *B01L 2200/0668* (2013.01); *B01L 2300/0681* (2013.01); *B01L 2300/123* (2013.01); *G01N 2001/4088* (2013.01)

(58) Field of Classification Search
CPC .......... B01D 39/1692; B01D 2239/065; B01D 33/015; B01D 33/01; B01D 25/003; B01D 25/12; B01D 2201/202; B01D 2201/186; B01D 33/0158; B01D 33/0183; B01D 25/26; B01D 29/095; B01D 29/01; B01D 29/70; B01D 63/08; B01D 63/081; B01D 63/082; B01D 63/087; B01D 2239/0654; B01D 2239/069; B01L 3/50255; B01L 2300/0681; B01L 2200/0668; B01L 2300/123; B01L 3/505; C12Q 1/24; G01N 2001/4088
See application file for complete search history.

(56) References Cited

U.S. PATENT DOCUMENTS

| | | | |
|---|---|---|---|
| 5,281,370 A * | 1/1994 | Asher | B82Y 20/00 264/1.1 |
| 5,711,884 A * | 1/1998 | Asher | G02B 6/1225 210/650 |
| 6,414,043 B1* | 7/2002 | Asher | B01J 13/0065 521/142 |
| 7,736,907 B2* | 6/2010 | Blankenstein | B01L 3/502723 436/177 |
| 7,981,345 B2* | 7/2011 | Yoo | B29C 45/14336 264/259 |
| 8,834,794 B2 | 9/2014 | Yazdanpanah et al. | |
| 8,951,732 B2* | 2/2015 | Pollack | C12Q 1/6846 435/6.12 |
| 9,205,432 B2* | 12/2015 | Chang | B03C 1/288 |
| 10,717,052 B2* | 7/2020 | Kim | B01D 69/12 |
| 10,987,754 B1* | 4/2021 | Eller | B23K 20/1275 |
| 2006/0273003 A1* | 12/2006 | Sudo | B01D 65/00 210/498 |
| 2007/0269893 A1 | 11/2007 | Blankenstein et al. | |
| 2008/0197065 A1* | 8/2008 | Wingo | B01D 39/1661 210/198.2 |
| 2012/0129192 A1* | 5/2012 | Yazdanpanah | C12M 41/36 435/7.23 |
| 2013/0288360 A1* | 10/2013 | Jeon | G01N 1/34 435/309.1 |
| 2015/0001147 A1* | 1/2015 | Leuthold | B01D 63/082 210/335 |
| 2016/0017274 A1* | 1/2016 | Pflanz | C12M 47/06 435/30 |
| 2016/0252436 A1* | 9/2016 | Jeon | G01N 1/34 435/308.1 |

* cited by examiner

FILTER DEVICE FOR CAPTURING TARGET CELL AND TARGET CELL COLLECTING METHOD USING THE SAME

TECHNICAL FIELD

The present invention relates to a filter device for capturing a target cell and a target cell collecting method using the same, and more particularly, to a filter device for capturing a target cell and a target cell collecting method using the same, which may easily collect a captured target cell.

BACKGROUND ART

A tumor cell is derived from an origin tumor mass in an initial stage of malignant progression.

Metastasis may occur when a part of such a cell moves from a place that is anatomically far away from the origin tumor mass through peripheral blood to form a new tumor.

Such metastasis is the most common cause of cancer-related deaths in solid tumor patients. Circulating tumor cells (hereinafter, referred to as "CTCs") circulating in a bloodstream are a main cause of the metastasis, and detection of such tumor cells is a method that is useful in diagnosis and clinical management of cancer patients, and a therapeutic effect may be predicted through the detection before the metastasis occurs.

However, since one to five CTCs exist per 100 million normal blood cells, which is very rare, it is difficult to detect the CTCs.

As described above, an example of a technology for detecting a CTC corresponds to a method of detecting and quantifying a tumor cell circulating in peripheral blood. Such a method may be classified into an affinity-based technology corresponding to a circulating antibody-based detection technology and a non-affinity-based technology in which separation is performed by a physical element, except for a nucleic acid-based detection technology requiring some manual preprocessing.

In general, the antibody-based technology uses microstructures doped with endothelial cell adhesion molecule (Ep-CAM) antibodies to capture circulating tumor cells.

Further, in this regard, although researches on various structural materials and coating methods and researches for finding antibodies having more higher affinities have been progressed to increase a deficient affinity between the antibody and the tumor cell, such an affinity-based detection method has a problem in that contact between a cell and the antibody is not perfect.

Thus, although a method of changing the shape of a structure coated with an antibody or adjusting flow of cells or a device for collecting a tumor cell captured by an antibody to analyze the tumor cell has been developed to solve such problems, the method is complex and a capture rate is still low.

In addition, although yet another method using an affinity corresponds to a technology using an antibody-coated magnetized bead, which is an FDA-approved tumor cell detection technology, there are problems in that the antibody-coated magnetized bead is hardly uniformly adhered to the tumor cell, and the magnetized bead attached to the cell does not respond well to a magnet.

Also, there are disadvantages in that some tumor cells cannot be detected due to characteristics of the antibody or small blood cells are also captured.

Meanwhile, an example of a technique not using an antibody corresponds to a method of individually separating a tumor cell by a filter according to the size of the tumor cell, which is generally larger than that of a blood cell.

However, such a filter has a problem in that since the filter is manufactured in the form of a thin film, shape maintaining force is low, and thus handling is difficult.

Also, there is a problem in that a target cell captured by the filter is not well separated from the filter.

DISCLOSURE

Technical Problem

An exemplary embodiment of the present invention provides a filter device for capturing a target cell, in which after a target cell is captured in a state in which the size of a lattice hole formed in a filter substrate is reduced, the size of the lattice hole is restored when the target cell is collected, so that a collect rate may be improved due to easy separation of the target cell from the filter substrate, and a collecting method using the same.

Also, another embodiment of the present invention provides a filter device for capturing a target cell in which as the size of a lattice hole is reduced, a contact area between the lattice hole and a target cell increases, so that a destruction rate of the target cell is reduced, and thus a collect rate may be improved, and a collecting method using the same.

Also, yet another embodiment of the present invention provides a filter device for capturing a target cell, in which since one surface of a filter substrate is maintained supported by a support substrate, a shape maintaining force increases, and thus handling is easy, and a collecting method using the same.

Technical Solution

A filter device for capturing a target cell according to an embodiment of the present invention may include a filter substrate formed of an elastic material and a plurality of lattice holes arranged in the filter substrate, in which when a specimen including a target cell passes through the filter substrate, the filter substrate is elastically compressed in one of a direction in which the lattice holes are formed and a direction intersecting with the direction in which the lattice holes are formed, so that the size of the lattice holes is reduced.

The filter device may further include a support substrate installed to be in contact with one surface of the filter substrate, and a pressing portion installed to press the other surface of the filter substrate.

The filter device may further include a filter structure in which the plurality of filter substrates are stacked in parallel to each other, a support substrate installed to be in contact with one surface of the filter structure, and a pressing portion installed to press the other surface of the filter structure.

When the lattice holes are formed in a lateral direction of the filter substrate, the pressing portion may be installed to press the filter substrate in a thickness direction of the filter substrate.

When the lattice holes are formed on a thickness direction surface of the filter substrate, the pressing portion may include a pressing member arranged to face the filter substrate in a face-to-face manner, having an inlet port through which the specimen is injected, and having a spread groove formed on a surface facing the filter substrate, and a plurality of pressing columns formed on a surface of the pressing member, which faces the filter substrate, and formed to be in contact with upper ends of edge walls of the lattice holes of the filter substrate.

The filter substrate may include at least one selected from the group consisting of polydimethylsiloxane (PDMS), polyurethane, latex, Ecoflex, hydrogel, epoxy resin, rubber, and elastic fiber.

When the filter substrate is elastically compressed, edge walls of the lattice holes may be elastically compressed such that central portions become convex in a direction intersecting an applied force.

The size of the lattice holes may be formed to correspond to the size of the target cell.

In the filter substrate, dummy holes may be further formed outside the lattice holes located on the outmost side among the arranged lattice holes. A target cell collecting method using a filter device for capturing a target cell may include positioning a filter substrate formed of an elastic material and having a plurality of lattice holes arranged in the filter substrate, to be in contact with one surface of the support substrate, reducing a size of the lattice holes by elastically compressing edges walls defining the lattice holes by applying a surface pressure to an entire surface of the filter substrate through a pressing portion, capturing a target cell by allowing a specimen including the target cell to pass through the lattice holes of the filter substrate, when the specimen completely passes through the lattice holes, restoring the size of the lattice holes by elastically restoring edge walls of the lattice holes by releasing the surface pressure applied by the pressing portion, and collecting the target cell captured by the lattice holes of the filter substrate.

The positioning of the filter substrate to be in contact with the one surface of the support substrate may include forming a filter structure in which the filter substrates are stacked in parallel to each other.

When the target cell captured by the lattice holes is collected, a fluid may flow in a forward direction or a reverse direction of a direction in which the specimen passes, so that the target cell is collected. At this time, the fluid may be a cell buffer.

Advantageous Effects

According to an embodiment of the present invention, after a target cell is captured in a state in which the size of a lattice hole formed in a filter substrate is reduced, the size of the lattice hole is restored when the target cell is collected, and thus the target cell is easily separated from the filter substrate, so that a collect rate may be improved.

Also, as the size of the lattice hole is reduced, a contact area between the lattice hole and the target cell increases, so that a destruction rate of the target cell is reduced, and thus a collect rate may be improved.

Also, since one surface of the filter substrate is maintained supported by a support substrate, a shape maintaining force increases, and thus handling is easy.

MODE FOR INVENTION

Figure 1:
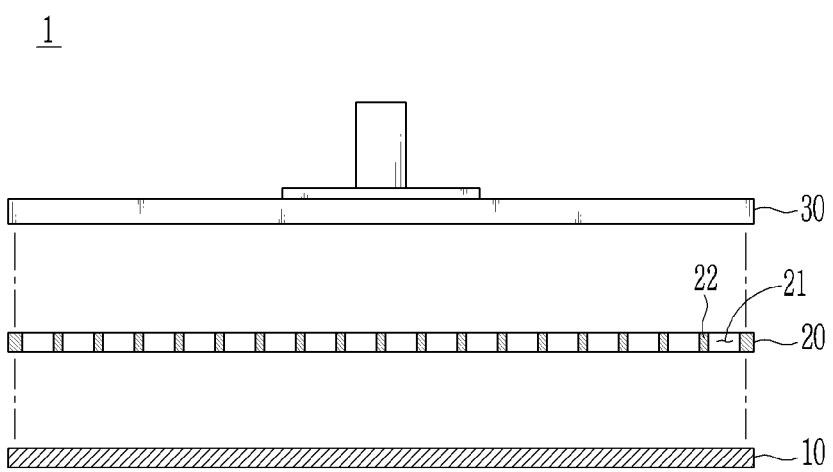
FIG. 1 is a schematic view illustrating a filter device for capturing a target cell according to a first embodiment of the present invention.

Hereinafter, embodiments of the present invention will be described in detail with reference to the accompanying drawings such that those skilled in the art to which the present invention pertains may easily implement the present invention. As those skilled in the art would realize, the described embodiments may be modified in various different ways, all without departing from the spirit or scope of the present invention.

In order to clearly illustrate the present invention, portions not related to the description are omitted in the drawings. Like reference numerals designate like elements throughout the specification.

Throughout this specification, when it is described that a first element is "coupled" to a second element, the first element may be "indirectly connected" to the second element with a third element interposed therebetween as well as the first element may be "directly connected" to the second element. Also, unless explicitly described to the contrary, the word "comprise" and variations such as "comprises" or "comprising", will be understood to imply the inclusion of stated elements but not the exclusion of any other elements.

Before description, in various embodiments, components having the same configurations will be typically described in a first embodiment, and the other components which are different from the first embodiment will be described in other embodiments.

Hereinafter, a filter device for capturing a target cell according to the first embodiment of the present invention will be described in detail with reference to the accompanying drawings.

FIG. 1 is a schematic view illustrating a filter device for capturing a target cell according to the first embodiment of the present invention. Referring to FIG. 1, a filter device 1 for capturing a target cell according to the first embodiment of the present invention includes a support substrate 10, a filter substrate 20, and a pressing portion 30.

The support substrate 10 may be formed plastic or glass, and may have a plurality of holes (not illustrated) through which blood may pass.

Figure 2:
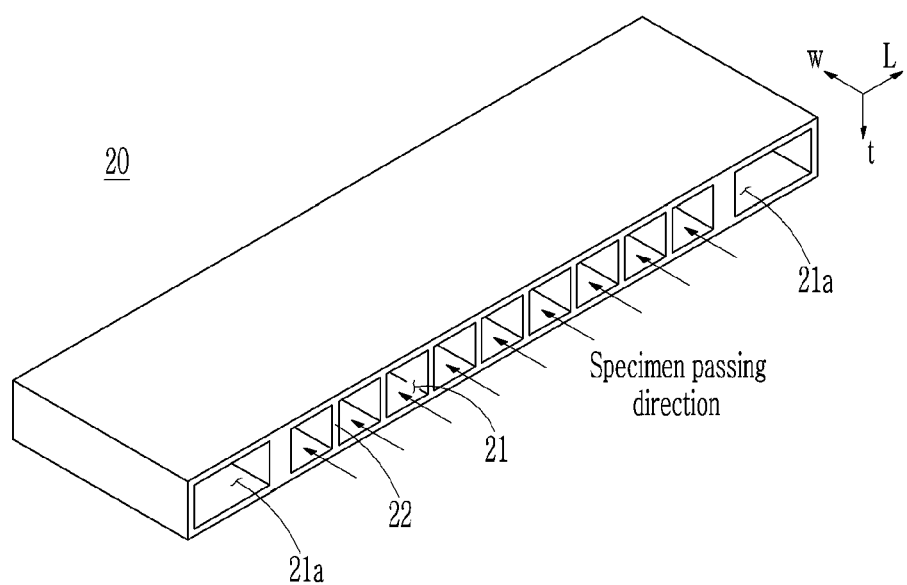
FIG. 2 is a perspective view illustrating a filter substrate of FIG. 1.

FIG. 2 is a perspective view illustrating a filter substrate of FIG. 1. Referring to FIG. 2, the filter substrate 20 is provided to have an approximately rectangular shape, and is located to be in contact with the upper surface of the support substrate 10.

The filter substrate 20 may include at least one selected from the group consisting of polydimethylsiloxane (PDMS), polyurethane, latex, Ecoflex, hydrogel, epoxy resin, rubber, elastic fiber, and the like, as elastic materials.

A plurality of lattice holes 21 and a plurality of dummy holes 21a are formed through the filter substrate 20 in a lateral direction w. The plurality of lattice holes 12 has a circular or polygonal cross section, and are arranged along a lengthwise direction L, and the dummy holes 21a are formed outside the lattice holes 21 located at the outmost side.

Here, the lattice holes 21 have a size corresponding to the size (the diameter) of a target cell, and when the filter substrate 20 is elastically compressed by the pressing portion 30, which will be described below, the target cell may be captured by the lattice holes 21.

The dummy holes 21a have a circular or polygonal cross section, are areas through which a specimen does not pass, and have a size that is larger than, smaller than, or equal to the size of the lattice holes 21 as needed. As illustrated, the size of the dummy holes 21a is larger than the size of the lattice holes 21.

The dummy holes 21a function to compensate for distortion of wall surfaces of the lattice holes 21 located at the outmost side due to a pressing force applied by the pressing portion 30.

That is, when the pressing force is applied by the pressing portion 30, the lattice holes 21 located on the outmost side are not elastically compressed such that central portions thereof in a longitudinal direction are deformed convexly but are somewhat irregularly deformed, which is unlike the other lattice holes 21 located on the inner side.

At this time, the dummy holes 21 and the lattice holes 21 are located on opposite sides of the outmost wall surfaces of the lattice holes 21 located on the outmost side, thereby guaranteeing uniform elastic compression deformation of the wall surfaces up to the outermost lattice holes 21.

The pressing portion 30 is provided to have a plate shape, is arranged to face the filter substrate 20 in a face-to-face manner, and is installed such that a surface pressure is applied or released in a thickness direction (a direction t of FIG. 2) of the filter substrate 20 (see FIG. 1).

When the surface pressure is applied to the filter substrate 20 by the pressing portion 30, edge walls 22 forming the lattice holes 21 of the filter substrate 20 are elastically compressed such that central portions thereof in a longitudinal direction become convex on opposite sides thereof.

Also, the surface pressure is released by the pressing portion 30, the edge walls 22 forming the lattice holes 21 of the filter substrate 20 are elastically restored.

Figure 3:
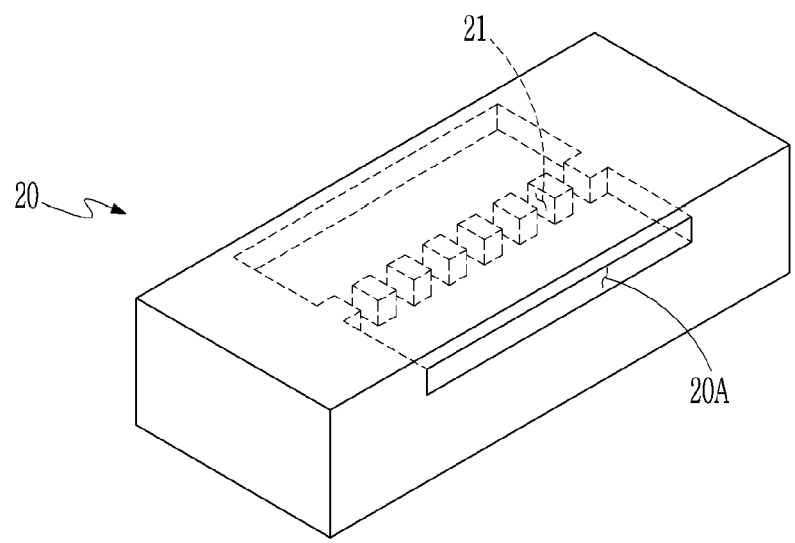
FIGS. 3 and 4 are schematic views illustrating the filter substrate of the filter device for capturing a target cell according to a variation of the first embodiment.
Figure 4:
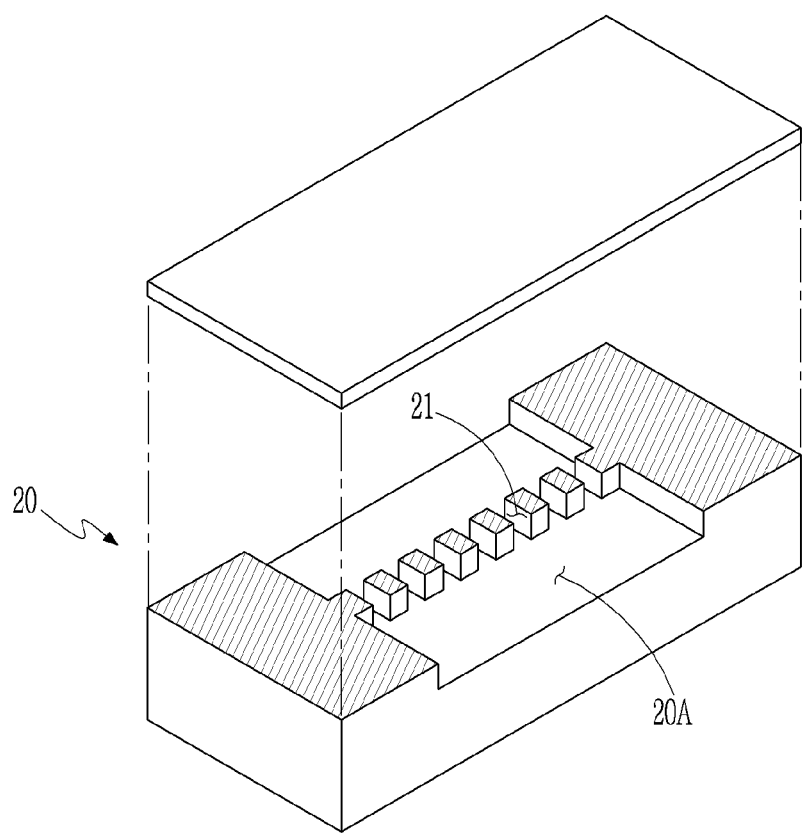

Although it has been described above that the lattice holes 21 are formed in the filter substrate 20, as illustrated in FIGS. 3 and 4, a channel 20A through which the specimen including the target cell may pass may be formed in the filter substrate 20, and the lattice holes 21 may be formed in the channel 20A.

From now on, a target cell collecting method using the above-described filter device for capturing a target cell according to the first embodiment of the present invention will be described.

FIGS. 5 to 8 are operating state diagrams according to a target cell collecting method using the filter device for capturing a target cell according to the first embodiment of the present invention.

Figure 5:
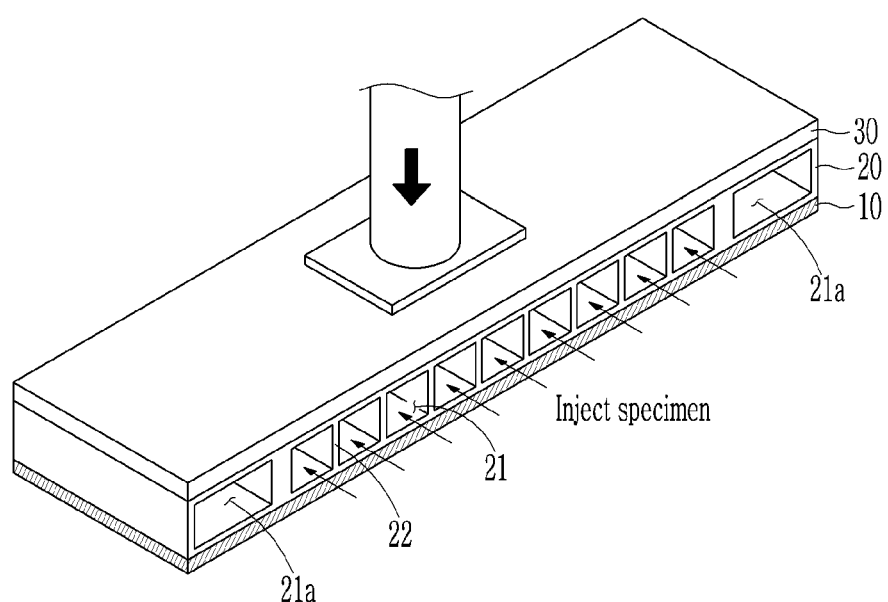
FIGS. 5 to 8 are operating state diagrams according to a target cell collecting method using the filter device for capturing a target cell according to the first embodiment of the present invention.

First, as illustrated in FIG. 5, the filter substrate 20 formed of an elastic material and having the lattice holes 21 arranged therein comes into contact with one surface of the support substrate 10, and the pressing portion 30 comes into contact with the filter substrate 20.

Figure 6:
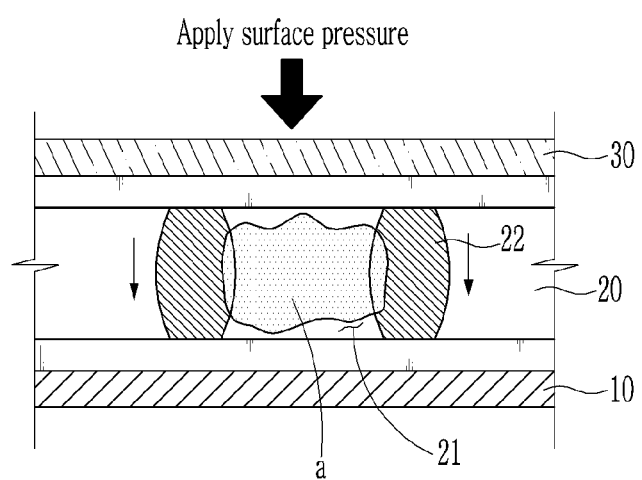

Further, when the surface pressure is applied to the filter substrate 20 through the pressing portion 30, as illustrated in FIG. 6, the edge walls 22 of the lattice holes 21 of the filter substrate 20 are elastically compressed so that the central portions thereof in the longitudinal direction become convex while curved surfaces are formed in an inward direction of the lattice holes 21. Accordingly, the size of the lattice holes 21 is reduced.

In this state, when a specimen including a target cell a is injected to pass through the filter substrate 20, the target cell a in the specimen including the target cell a is caught and captured by the lattice hole 21 which is elastically compressed and thus reduced. For example, when the specimen is blood, the target cell a may be a cancer cell that is larger than other cells constituting the blood.

At this time, even in a state in which the target cell a is caught by the lattice hole 21, a force is applied to the target cell a by the specimen passing through a portion where the target cell a is not located. However, like a situation in which the target cell a is forcibly fitted and caught in the reduced lattice hole 21, a force which the lattice hole 21 may withstand without being destroyed increases as a contact area between the target cell a and the lattice hole 21 gradually increases.

Figure 7:
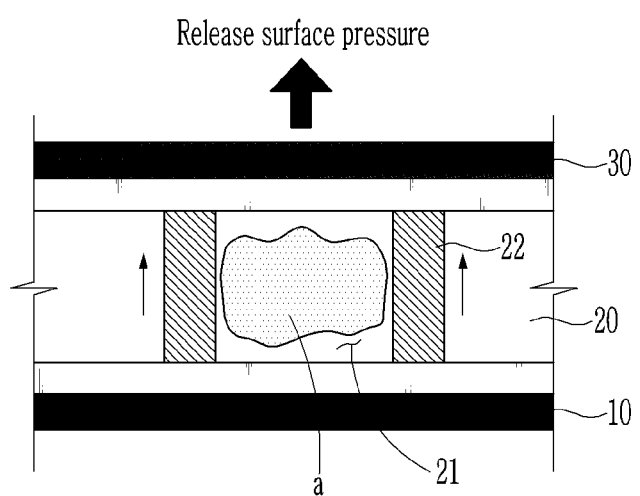

Further, after all the specimen including the target cell a completely passes through the filter substrate 20, the surface pressure applied to the filter substrate 20 through the pressing portion 30 is released. Through this, as illustrated in FIG. 7, the edge walls 22 of the lattice holes 21 are elastically restored so that the size of the lattice holes 21 are restored.

Figure 8:
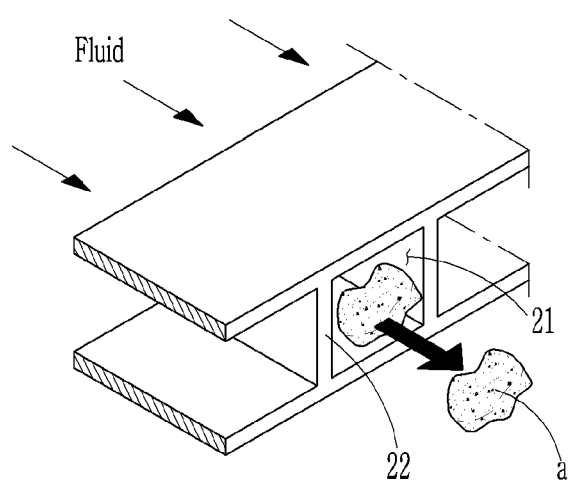

Next, the filter substrate 20 is separated from the support substrate 10, and as illustrated in FIG. 8, a predetermined amount of fluid flows in a forward direction or a reverse direction with respect to a direction in which the specimen passes, so that the target cell is easily removed from the lattice hole 21 and is thus collected. It is illustrated that the fluid flows in the reverse direction, and the removal may be performed by spraying the fluid through a blower or the like as needed.

A cell buffer such as Phosphate Buffered Saline (PBS) and N-2-Hydroxyethylpiperazine-N'-2-ethanesulfonic acid (HEPES) may be used as the fluid.

Through this, the target cell that has not been collected since the target cell is caught by the lattice hole 21 may be collected, so that a collect rate may be improved.

Also, as compared with the related art in which the target cell caught by the lattice hole 21 is destroyed while being separated from the lattice hole 21, the target cell is easily removed from the lattice hole 21 so that the target cell may be prevented from being damaged.

Next, a filter device for capturing a target cell according to a second embodiment of the present invention will be described. In the second embodiment of the present invention, a formation direction of a lattice hole of a filter substrate and a configuration of a pressing portion are partially changed. The filter device for capturing a target cell according to the second embodiment of the present invention includes the support substrate 10, the filter substrate 20, and the pressing portion 30, as illustrated in FIG. 1. Since the support substrate 10 has the same configuration as that according to the first embodiment, detailed description thereof will be omitted.

Figure 9:
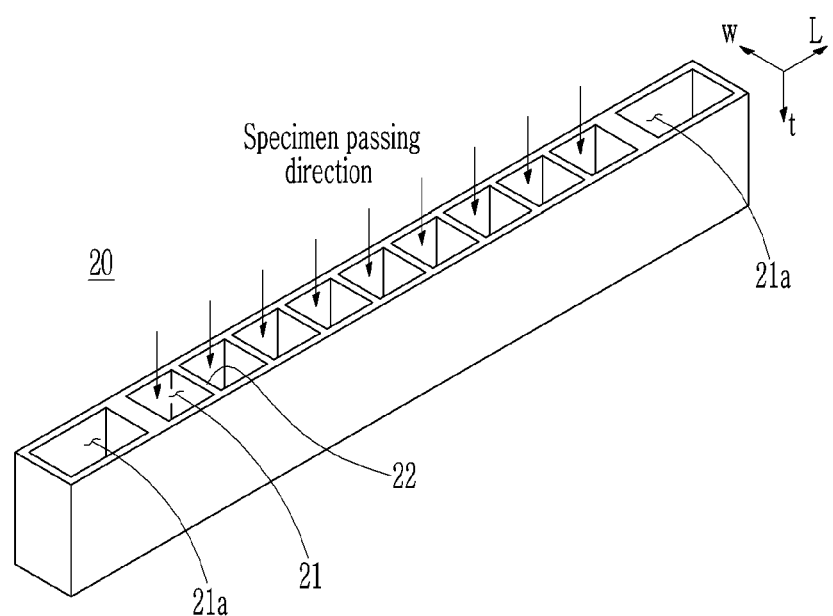
FIG. 9 is a perspective view illustrating a filter substrate of a filter device for capturing a target cell according to a second embodiment of the present invention.

FIG. 9 is a perspective view illustrating the filter substrate 20 of the filter device for capturing a target cell according to the second embodiment of the present invention. Referring to FIG. 9, the filter substrate 20 is provided in an approximately rectangular shape, and is located to be in contact with the upper surface of the support substrate 10.

A plurality of lattice holes 21 and a plurality of dummy holes 21a are formed through the filter substrate 20 in a thickness direction t of the filter substrate 20, which is a direction in which a specimen passes. The plurality of lattice holes 21 are arranged along a lengthwise direction L, and the dummy holes 21a are formed outside the lattice holes 21 located on the outmost side. Only formation directions of the lattice holes 21 and the dummy holes 21a are different from those according to the first embodiment, and the materials, the sizes, and the like thereof are the same as those according to the first embodiment.

Figure 10:
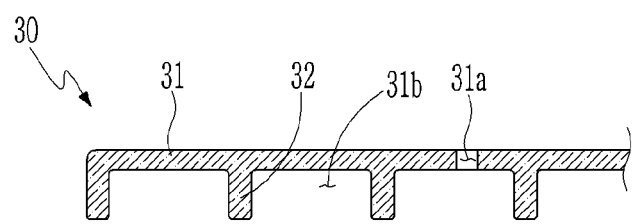
FIG. 10 is a detailed view illustrating a pressing portion of the filter device for capturing a target cell according to the second embodiment of the present invention.

FIG. 10 is a detailed view illustrating a pressing portion of the filter device for capturing a target cell according to the second embodiment of the present invention. Referring to FIG. 10, the pressing portion 30 includes a pressing member 31 and pressing columns 32.

The pressing member 31 is arranged to face the filter substrate 20 in a face-to-face manner, has an inlet port 31a through which blood may be injected, and has a spread groove 31b formed on a surface facing the filter substrate 20. That is, the pressing member 31 is formed to have a shape that is similar to a cap shape.

The plurality of pressing columns 32 is arranged on a surface of the pressing member 31, which faces the filter substrate 20, to be spaced apart from each other, and the height of the pressing columns 32 is formed to be in contact with upper ends of edge walls 22 of the lattice holes 21 of the filter substrate 20 when the filter substrate 20 is pressed.

Also, the pressing columns 32 are formed to be in contact with parts of upper surfaces of the edge walls 22 of the lattice holes 21 such that blood injected through the inlet port 31a may be injected into the filter substrate 20.

When the specimen including the target cell a passes through the filter substrate 20, such pressing portions 30 apply a surface pressure which is applied to the entire surface of the filter substrate 20. That is, the edge walls 22 defining the lattice holes 21 of the filter substrate 20 are elastically compressed by the applied surface pressure so that the size of the lattice holes 21 is reduced.

Also, after the specimen including the target cell a completely passes through the filter substrate 20, the pressing portions 30 release the surface pressure applied to the filter substrate 20. That is, when the surface pressure is released, the elastically compressed edge walls 22 of the lattice holes 21 are elastically restored so that the size of the lattice holes 21 is restored.

Even in the above-described second embodiment, a channel is formed in the filter substrate 20, and a plurality of lattice holes may be formed in the channel, which is like the first embodiment.

From now on, a target cell collecting method using the above-described filter device for capturing a target cell according to the present invention will be described.

FIGS. 11 to 14 are operating state diagrams according to a target cell collecting method using the filter device for capturing a target cell according to the first embodiment of the present invention.

Figure 11:
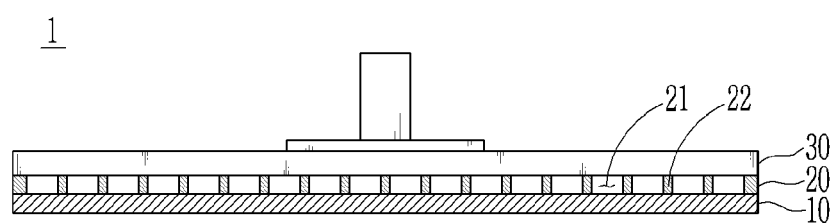
FIGS. 11 to 14 are operating state diagrams according to a target cell collecting method using the filter device for capturing a target cell according to the second embodiment of the present invention.

First, as illustrated in FIG. 11, the filter substrate 20 formed of an elastic material and having the lattice holes 21 arranged therein is in contact with one surface of the support substrate 10, and the pressing portion 30 is located to be in contact with the filter substrate 20.

Figure 12:
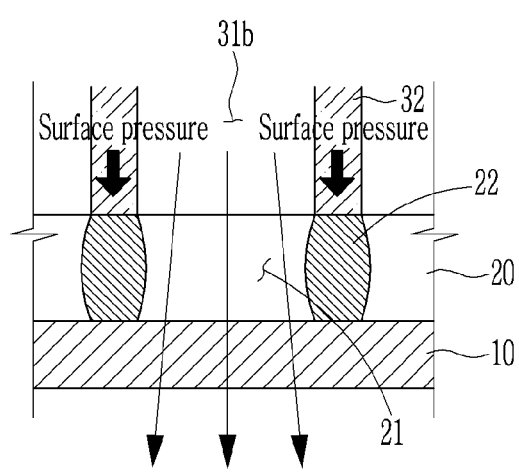

Further, as illustrated in FIG. 12, when a surface pressure is applied to the filter substrate 20 through the pressing columns 32 of the pressing portion 30, the edge walls 22 of the lattice holes 21 of the filter substrate 20 are elastically compressed so that central portions thereof in a longitudinal direction become convex while curved surfaces are formed in an inward direction of the lattice holes 21. Accordingly, the size of the lattice holes 21 is reduced.

Figure 13:
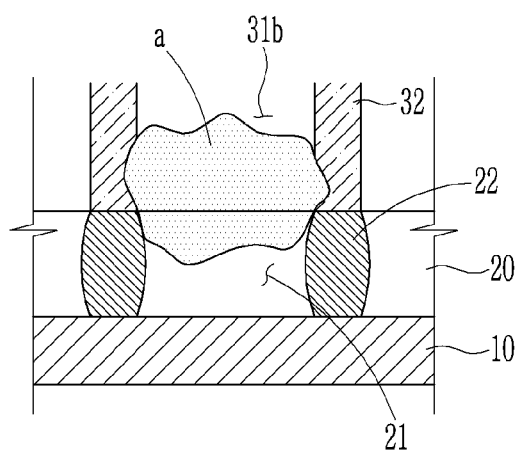

In this state, when the specimen including the target cell a is injected through the filter substrate 20, as illustrated in FIG. 13, the target cell in the specimen including the target cell a is caught and captured by the lattice hole 21, which is elastically compressed and is thus reduced. For example, when the specimen is blood, the target cell a may be a cancer cell that is larger than other cells constituting the blood.

At this time, even in a state in which the target cell a is caught by the lattice hole 21, a force is applied to the target cell a by the specimen passing through a portion where the target cell a is not located. However, like a situation in which the target cell a is forcibly fitted and caught in the reduced lattice hole 21, a force which the lattice hole 21 may withstand without being destroyed increases as a contact area between the target cell a and the lattice hole 21 gradually increases.

Figure 14:
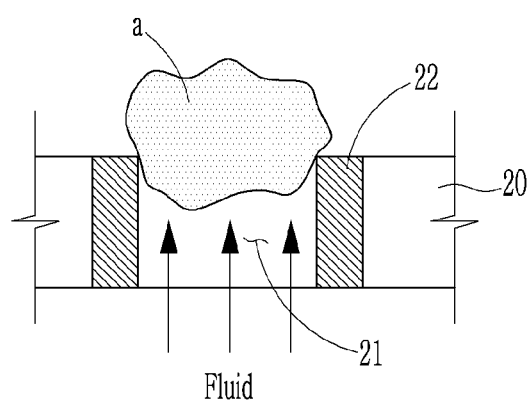

Further, after all the specimen including the target cell a completely passes through the filter substrate 20, the surface pressure applied to the filter substrate 20 through the pressing portion 30 is released. Through this, as illustrated in FIG. 14, the edge walls 22 of the lattice holes 21 are elastically restored so that the size of the lattice holes 21 is restored.

Next, the filter substrate 20 is separated from the support substrate 10, and when a fluid such as a cell buffer flows in a forward direction or a reverse direction with respect to a direction in which the specimen passes, in a direction that is opposite to a direction in which the surface pressure of the pressing portion 30 is applied, the target cell a is easily removed from the lattice hole 21 and is thus collected.

Through this, the target cell that has not been collected since the target cell a is caught by the lattice hole 21 may be collected, so that a collect rate may be improved.

Also, as compared with the related art in which the target cell caught by the lattice hole 21 is destroyed while being separated from the lattice hole 21, the target cell a is easily removed from the lattice hole 21 so that the target cell a may be prevented from being damaged.

Figure 15:
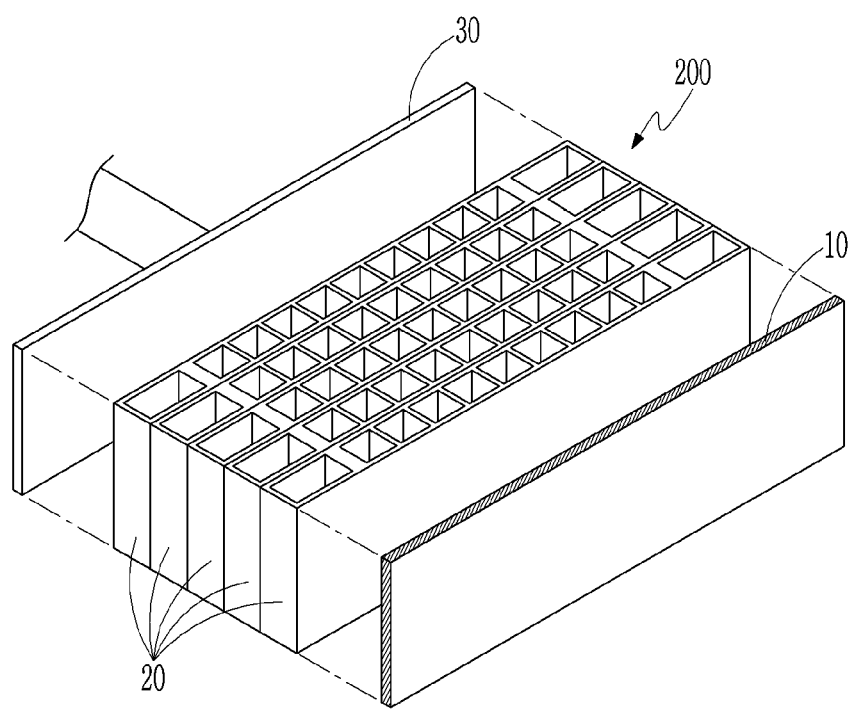
FIG. 15 is a schematic view illustrating a filter device for capturing a target cell according to a third embodiment of the present invention.
Figure 16:
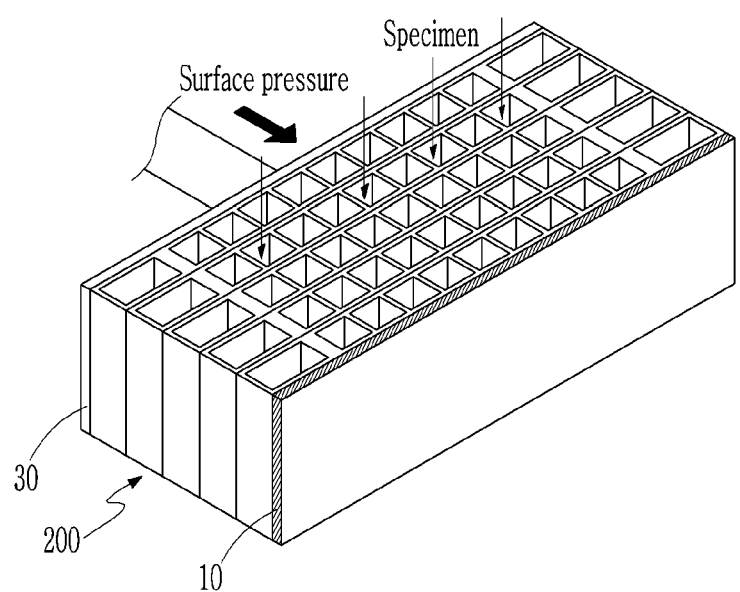
FIG. 16 is an operating state diagram of FIG. 15.

Next, a filter device for capturing a target cell according to a third embodiment of the present invention will be described. FIG. 15 is a schematic view illustrating a filter device for capturing a target cell according to a third embodiment of the present invention. Referring to FIG. 15, the filter device for capturing a target cell according to the third embodiment of the present invention includes a filter structure 200 in which a plurality of filter substrates 20 are stacked in parallel to each other, the support substrate 10, and the pressing portion 30.

In the filter structure 200, the plurality of filter substrates 20 according to the first embodiment are stacked in parallel to each other. Further, the support substrate 10 is located to be in contact with the outmost one surface of the filter structure 200, and the pressing portion 30 is located to be in contact with the outmost other surface of the filter structure 200. At this time, the support substrate 10 may be substituted for the pressing portion 30.

In the above state, as in the above-described first embodiment and the above-described second embodiment, after a surface pressure is applied to the filter structure 200 through the pressing portion 30, the specimen passes through the filter structure 200 so that the target cell may be captured through the lattice holes, the size of which is reduced. In a collecting process, after the surface pressure by the pressing portion 30 is released, a fluid such as a cell buffer flows in a forward direction or a reverse direction with respect to a direction in which the specimen passes, so that the target cell may be collected.

Meanwhile, it is illustrated in the third embodiment that the filter structure in which the filter substrates according to the first embodiment are stacked on each other. Even when the filter substrates having channels formed therein and the plurality of lattice holes is formed therein are used, the same effect may be achieved.

The scope of the present invention is not limited to the above-described embodiments, and the present invention may be implemented in various embodiments within the appended claims. It can be understood by those skilled in the art to which the present invention pertains that various modifications are included in the scope of the appended claims of the present invention without departing from the subject matter of the present invention claimed by the appended claims.

<Description of symbols>

| | |
|---|---|
| 1: Filter device for capturing target cell | |
| 10: Support substrate | |
| 20: Filter substrate | 21: Lattice hole |
| 21a: Dummy hole | 22: Edge wall |
| 200: Filter structure | |
| 30: Pressing portion | 31: Pressing member |
| 31a: Inlet port | 31b: Spread groove |
| 32: Pressing column | |

The invention claimed is:

1. A filter device for capturing a target cell included in a specimen, the filter device comprising:
   a filter substrate formed of an elastic material; and
   a plurality of lattice holes arranged in the filter substrate;
   dummy holes disposed on opposing sides of the lattice holes in the filter substrate, wherein the lattice holes are arranged in a line between the dummy holes,
   wherein under application of a pressure to the filter substrate, a structure of the filter substrate is elastically compressed in a first direction in which the lattice holes penetrate the filter substrate or a second direction intersecting the first direction, so that a size of the lattice holes is reduced, and
   wherein the dummy holes do not allow the specimen passing through.

2. The filter device of claim 1, further comprising:
   a support substrate installed to be in contact with one surface of the filter substrate; and
   a pressing portion installed to press a surface of the filter substrate which is opposite of and faces the one surface.

3. The filter device of claim 2, wherein
   the lattice holes penetrate the filter substrate in a lateral direction, and
   the pressing portion is installed to press the filter substrate in a thickness direction of the filter substrate.

4. The filter device of claim 1, wherein
   the filter substrate is comprised in plural, and
   further comprising:
   a filter structure in which the plurality of filter substrates are stacked in parallel to each other;
   a support substrate installed to be in contact with one surface of the filter structure; and
   a pressing portion installed to press a surface of the filter structure which is opposite of and faces the one surface.

5. The filter device of claim 4, wherein
   the lattice holes penetrate the filter substrate in a lateral direction, and
   the pressing portion is installed to press the filter substrate in a thickness direction of the filter substrate.

6. The filter device of claim 1, wherein
   the filter substrate includes at least one material selected from the group consisting of polydimethylsiloxane (PDMS), polyurethane, latex, Ecoflex, hydrogel, epoxy resin, rubber, and elastic fiber.

7. The filter device of claim 1, wherein
   in a state that the structure of the filter substrate is elastically compressed, edge walls of the lattice holes are elastically compressed such that central portions become convex in a direction intersecting an applied force.

8. The filter device of claim 1, wherein
   the size of the lattice holes is formed to correspond to the size of the target cell.

9. A filter device for capturing a target cell included in a specimen, the filter device comprising:
   a filter substrate formed of an elastic material;
   a plurality of lattice holes arranged in the filter substrate;
   a support substrate installed to be in contact with one surface of the filter substrate; and
   a pressing portion installed to press a surface of the filter substrate which is opposite of and faces the one surface,
   wherein under application of a pressure to the filter substrate, a structure of the filter substrate is elastically compressed in a first direction in which the lattice holes penetrate the filter substrate or a second direction intersecting the first direction, so that a size of the lattice holes is reduced,
   wherein
   the lattice holes penetrate the filter substrate in a thickness direction,
   the pressing portion includes:
   a pressing member arranged to face the filter substrate in a face-to-face manner, having an inlet port through which the specimen is injected, and having a spread groove formed on a surface facing the filter substrate; and
   a plurality of pressing columns formed on a surface of the pressing member, which faces the filter substrate, and formed to be in contact with upper ends of edge walls of the lattice holes of the filter substrate.

* * * * *